United States Patent [19]

Geers, Jr.

[11] Patent Number: Plant 5,555

[45] Date of Patent: Sep. 10, 1985

[54] WEIGELA PLANT - GEENALTAN

[75] Inventor: Hermann Geers, Jr., Boskoop, Netherlands

[73] Assignee: The Conard-Pyle Company, West Grove, Pa.

[21] Appl. No.: 564,165

[22] Filed: Dec. 22, 1983

[51] Int. Cl.[3] ..... A01H 5/00

[52] U.S. Cl. ..... Plt./54

[58] Field of Search ..... Plt./54

*Primary Examiner*—Robert E. Bagwill

*Attorney, Agent, or Firm*—Burns, Doane, Swecker & Mathis

[57] ABSTRACT

A new and distinct variety of Weigela is provided which originated as a volunteer seedling in a planting of *Weigela florida* Eva Rathke variety at Boskoop, The Netherlands. The present variety exhibits a vigorous and truly dwarf growth habit and forms attractive crimson flowers in greater abundance and for a longer duration than *Weigela florida* Eva Rathke variety. Accordingly, the present variety can be used to advantage in smaller landscape settings while offering superior characteristics when compared to related previously known Weigela plants which are larger in size and which flower to a lesser degree.

1 Drawing Figure

SUMMARY OF THE INVENTION

My invention relates to a new, distinctive, and useful variety of Weigela which originated under cultivation in my nursery at Boskoop, The Netherlands. The new variety was selected from among seven volunteer seedlings found in an area where plants of *Weigela florida* Eva Rathke were being grown. Accordingly, it is assumed that the seed parent of the new variety is *Weigela florida* Eva Rathke. While the pollen parent of the new variety is unknown, it also was likely to be the Eva Rathke variety.

My interest in developing a new form of Weigela was based on the need for a more dwarf from of the plant, as all common Weigelas currently available in the trade tend to become too large, especially for today's smaller landscapes. The seven volunteer seedlings were discovered by me during the Spring of 1975 and were observed for three full seasons. In the Summer of 1978 one of these seedlings, bearing the desired dwarf characteristics, was selected and propagated by me. The resulting plants of this propagation were then observed for four years. During this time my belief that the present invention would remain dwarf was confirmed, since it did not exceed a height of more than approximately 70 cm. The new variety exhibits a combination of advantageous characteristics which distinguish it from all other forms of Weigela of which I am aware. For instance, plants of *Weigela florida* Eva Supreme, while smaller than *Weigela florida* Eva Rathke, are known to achieve a height of 5 feet.

The new and distinct variety of the present invention exhibits:

(a) a vigorous dwarf growth habit wherein the plant assumes only about one-third the size of *Weigela florida* Eva Rathke, and a size which is substantially smaller than that of *Weigela florida* Eva Supreme, (b) a deep crimson flower coloration which is very close to that of *Weigela florida* Eva Rathke, (c) a flower size which is very close to that of *Weigela florida* Eva Rathke, and (d) flower formation is greater abundance and for a longer duration than *Weigela florida* Eva Rathke, with said floriferousness commonly reaching its height during early to mid-June when grown at West Grove, Pa., and continuing thereafter though in moderation until frost.

Asexual reproduction of my new variety by softwood cuttings during the summer under mist at Boskoop, The Netherlands, and at West Grove, Pa. has demonstrated that the unique combination of characteristics of the new variety is fully established and transmitted to successive generations.

The new variety has been designated Geenaltan. The new variety will be marketed by the Conard-Pyle Company in the United States under the EVITA trademark.

BRIEF DESCRIPTION OF THE PHOTOGRAPH

The accompanying photograph shows a typical specimen of my new variety of Weigela as depicted in color as nearly true as it is reasonably possible to make the same in a color illustration of this character. It is apparent that the photograph tends to be slightly underexposed and that foliage of other plants such as *Yucca filamentosa* is visible in the background. The specimen illustrated was being grown out-of-doors during mid-June at Boskoop, The Netherlands.

The present photograph is substantially the same as that which appeared on the cover of *The Complete Garden Catalog* dated Spring 1983 which was distributed by The Wayside Gardens Co. of Hodges, S.C. 29695. That catalog through error specified the illustrated variety to be the Eva Supreme variety when it was in fact the Geenaltan variety of the present application.

DETAILED DESCRIPTION

The plants described were two year old plants growing out-of-doors in containers in a soilless growing medium at West Grove, Pa.

The chard utilized in the identification of the colors is that of The Royal Horticultural Society (R.H.S. Colour Chart).

Parentage: The seed parent is believed to be the Eva Rathke variety of *Weigela florida.* The pollen parent is unknown.

Plant:

*Type.*—Deciduous, compact, dwarf, flowering shrub, exhibits good vigor.

*Height.*—A maximum height of approximately 70 cm. has been achieved when grown at Boskoop, The Netherlands. It is believed that such maximum height will be similarly observed at West Grove, Pa.

Breadth.—A breadth of approximately one meter has been achieved when grown at Boskoop, The Netherlands. It is believed that such maximum breadth may be slightly exceeded when grown at West Grove, Pa.

Foliage:

*Shape.*—Ovate, with obtuse base, and acute apex.

*Size.*—The mature leaves are widely variable in size. They commonly range from approximately 5.0 to 9.5 cm. in length, and from approximately 1.5 to 4.0 cm. in width.

*Color.*—Fully expanded immature leaf: Upper surface is Green Group 143A, and the under surface is closest to, but greener than, Yellow-Green Group 148B. Mature leaf: Upper surface is closest to Green Group 135B, and the under surfae is closest to but greener than Yellow-Group 148A.

*Internode length.*—Extremely variable, and commonly ranges from approximately 0.7 to 4.0 cm.

Flower:

*Color.*—The bud immediately prior to the separation of the petals on both the interior and exterior petal surfaces is Red Group 46A. The flower two days after petal separation on both the interior and exterior petal surfaces varies between Red Group 46A and Red Group 53B. The stamens and stigma are virtually pure white in coloration.

*Size.*—Approximately 2.5 to 3.0 cm.

When borne.—The flowers are borne in abundance during early to mid-June, and continually thereafter though in moderation until frost.

Hardiness: No winter damage has been observed to data at West Grove, Pa.

I claim:

1. A new and distinct variety of Weigela, substantially as illustrated and described, characterized as to novelty by the following combination of characteristics:

(a) a vigorous dwarf growth habit wherein the plant assumes about one-third the size of *Weigela florida* Eva Rathke, and a size which is substantially smaller than that of *Weigela florida* Eva Supreme, (b) a deep crimson flower coloration which is very close to that of *Weigela florida* Eva Rathke, (c) a flower size which is very close to that of *Weigela florida* Eva Rathke, and (d) flower formation in a greater abundance and for a longer duration than *Weigela florida* Eva Rathke, with said floriferousness commonly reaching its height during early to mid-June when grown at West Grove, Pa., and continuing thereafter though in moderation until frost.

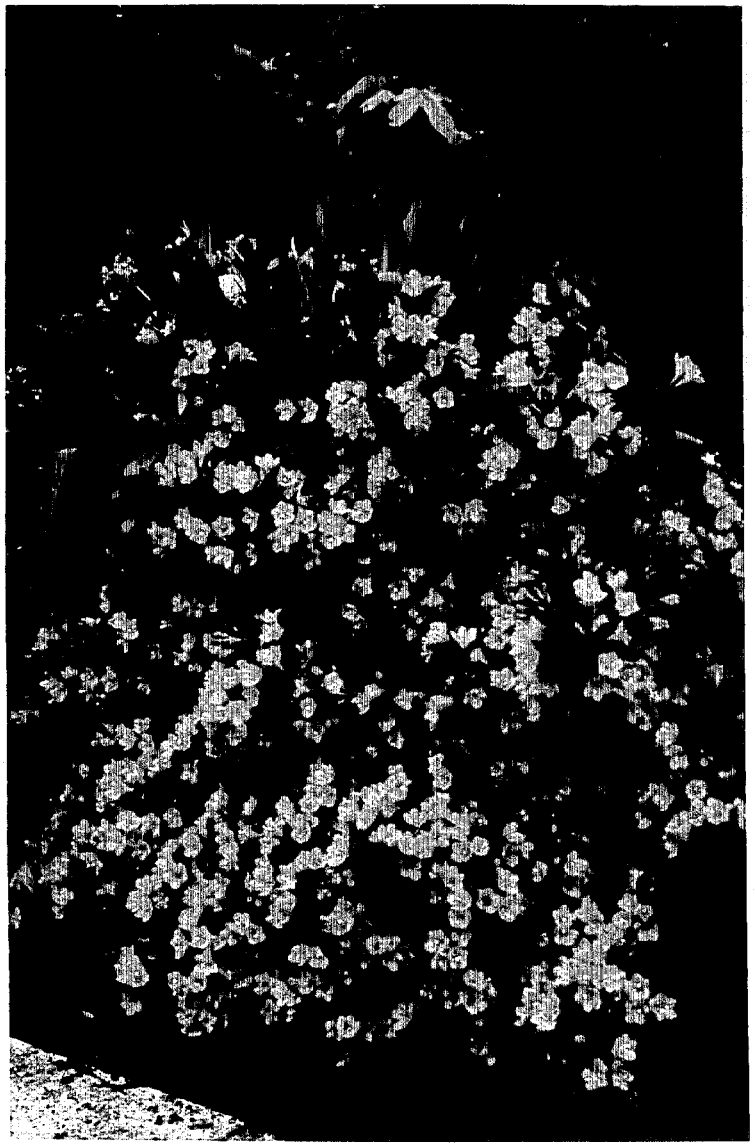

* * * * *